United States Patent [19]

Bigg

[11] 4,349,683
[45] Sep. 14, 1982

[54] THIAZOLIDINE-2,4-DIONE DERIVATIVES

[75] Inventor: Dennis C. Bigg, Marsillargues, France

[73] Assignee: Synthelabo, Paris, France

[21] Appl. No.: 181,475

[22] Filed: Aug. 26, 1980

Related U.S. Application Data

[63] Continuation of Ser. No. 914, Dec. 29, 1978, abandoned.

[30] Foreign Application Priority Data

Dec. 29, 1977 [FR] France .................. 77 39559
Nov. 24, 1978 [FR] France .................. 78 33244

[51] Int. Cl.³ .................................... C07D 277/04
[52] U.S. Cl. ................................. 548/183; 424/270; 548/154
[58] Field of Search ............... 548/182, 183; 424/270

[56] References Cited

FOREIGN PATENT DOCUMENTS 37-2620 5/1962 Japan .

Primary Examiner—Nicholas S. Rizzo
Attorney, Agent, or Firm—Wegner & Bretschneider

[57] ABSTRACT

Thiazolidine-2,4-dione derivatives, in the form of racemates or optically active isomers, corresponding to the formula (I)

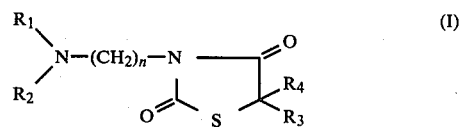

in which $n=2$ or 3, $R_1=H$, alkyl, benzoyl, acetyl or optionally substituted benzyl, $R_2=H$ or alkyl, $R_3=$phenyl, which is optionally substituted by halogen, alkyl, alkoxy, $NO_2$, $CF_3$ or $CF_3S$, or naphthyl, and $R_4=H$, alkyl, phenyl, benzoyl or allyl, and acid addition salts thereof.

These compounds are useful in therapy as anti-convulsants or anti-depressants.

6 Claims, No Drawings

THIAZOLIDINE-2,4-DIONE DERIVATIVES

This is a Continuation of application Ser. No. 914 filed Dec. 29, 1978, now abandoned.

DESCRIPTION

The present invention relates to thiazolidine-2,4-dione derivatives in the form of racemates or enantiomers, their addition salts with pharmaceutically acceptable acids, their preparation and their application in therapy.

The derivatives of the invention correspond to the formula (I)

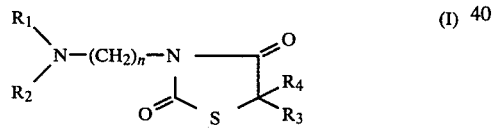

in which n is 2 or 3, $R_1$ is a hydrogen atom, an alkyl radical having 1 to 4 carbon atoms, the benzoyl radical, the acetyl radical, or the benzyl radical which may or may not carry a substituent chosen from amongst methyl or methoxy radicals and halogen atoms, $R_2$ is a hydrogen atom or an alkyl radical having 1 to 4 carbon atoms, $R_3$ is either a phenyl radical, which may or may not carry one or more substituents chosen from the group comprising halogen atoms, alkyl and alkoxy radicals having 1 to 4 carbon atoms, and the radicals $NO_2$, $CF_3$ and $CF_3S$, or a naphthyl radical, and $R_4$ is a hydrogen atom, an alkyl radical having 1 to 4 carbon atoms, the phenyl radical, the benzyl radical or the allyl radical, except for the compounds in which $R_3$ is $C_6H_5$ and $R_4$ is H when $R_1$ and $R_2$ are $CH_3$ and n is 2 or 3.

The addition salts of the compounds (I) with pharmaceutically acceptable acids form part of the invention.

The compounds of the invention contain an asymmetric carbon and can therefore give rise to two optically active isomers.

These isomers can be separated by any suitable method or prepared by stereospecific synthesis, and they form part of the invention.

The preferred compounds of the invention are those in which n is 2, and these include a particular group comprising the compounds in which $R_1$ and $R_2$ are H.

The alkyl and alkoxy radicals are preferably methyl and methoxy radicals.

According to the invention, the compounds are prepared in accordance with the following reaction scheme:

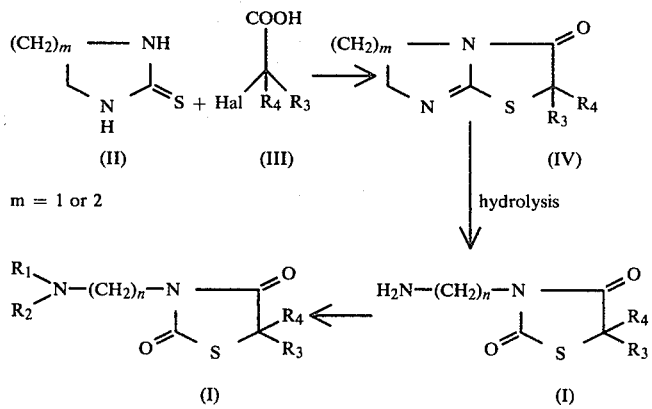

m = 1 or 2

The condensation of the compounds (II) and (III) is preferably carried out in acid at a temperature of 60° to 80° C.

When $R_4$ is H, the process of the invention consists in reacting the compound (II) with the compound (III)'

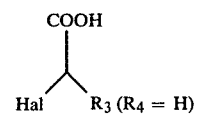

and then subjecting the resulting compound (IV)'

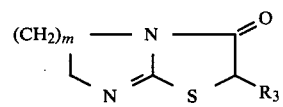

to diverse conversion reactions leading to the various compounds (I): see reaction scheme below.

1. Hydrolysis leading to (I) in which $R_1=R_2=R_4=H$, which can be alkylated to give the compound (I) in which $R_1$ and $R_2$ can be different from H;

2.1 substitution in the 2-position of the imidazo[2,1-b]thiazole ring by $R_4$, followed by hydrolysis leading to (I) in which $R_1=R_2=H$;

2.2 substitution in the 2-position of the imidazo[2,1-b]thiazole ring by $R_4$, followed by substitution on the nitrogen by $R_1$ and hydrolysis leading to (I) in which $R_2=H$; and 3. substitution on the nitrogen by $R_1$, followed by hydrolysis leading to (I) in which $R_2=R_4=H$.

The starting products (III)' are known.

The intermediates (IV) are new except for those in which $R_4$ is H, n=2 and $R_3$ is $C_6H_5$, 2—Cl—$C_6H_4$, 2,4-di—Cl—$C_6H_3$ and 3,4-di—Cl—$C_6H_3$.

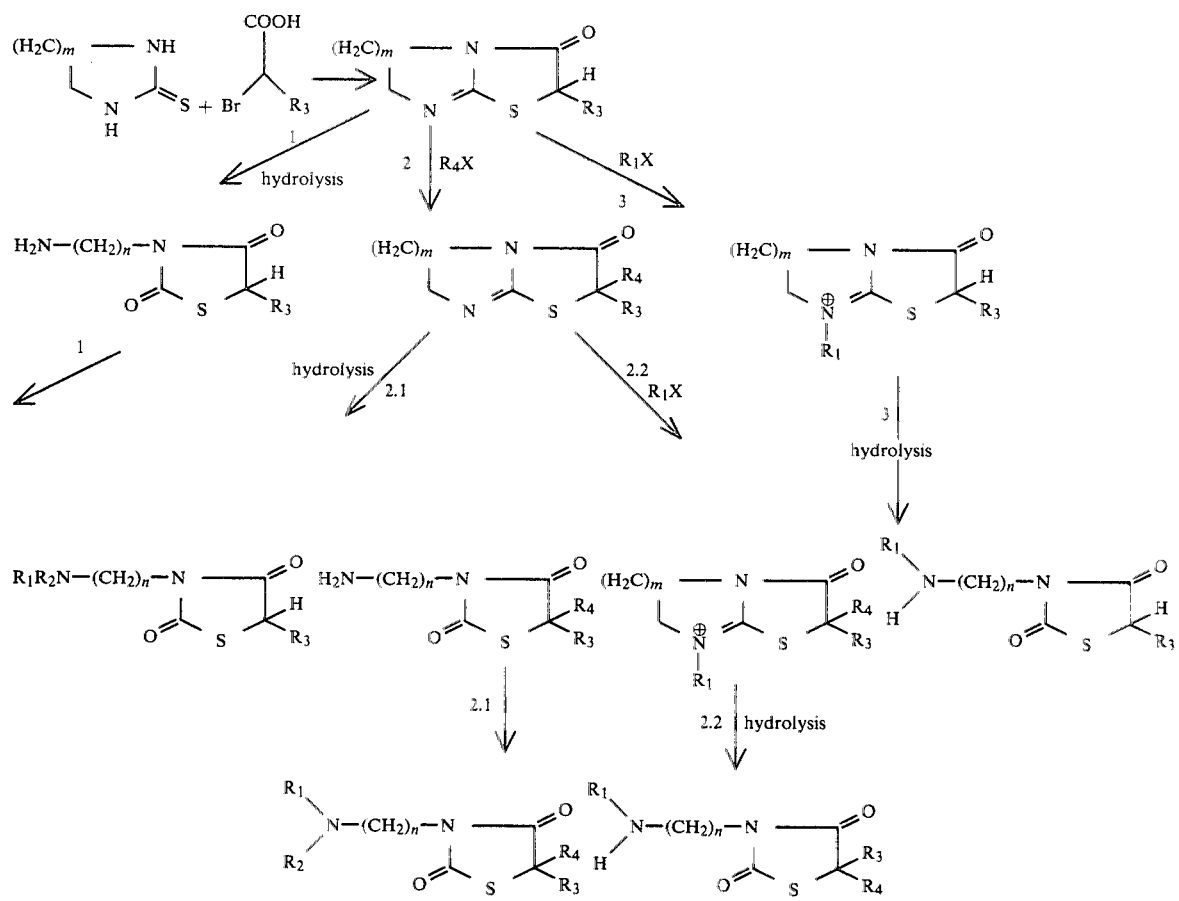

The following examples illustrate the invention.

The analyses and IR and NMR spectra confirm the structure of the compounds.

EXAMPLE 1
3-(2-Aminoethyl)-5-methyl-5-(4-fluorophenyl)thiazolidine-2,4-dione hydrobromide.

[$R_1=R_2=H$; $R_3=4-F-C_6H_4$; $R_4=CH_3$]

1.1  2-(p-Fluorophenyl)-2-methyl-5,6-dihydroimidazo[2,1-b]thiazol[2H]-3-one.

18.9 g (0.185 mol) of ethylene-thiourea and 45.8 g (0.185 mol) of α-bromo-α-methyl-(p-fluorophenyl)-acetic acid in 110 cm³ of acetic acid are introduced into a 1 liter round-bottomed flask.

The mixture is heated at 65°–75° C. for 4 hours until a clear solution is obtained. The solution is allowed to cool and is concentrated. An orange oil is recovered and taken up in acetone. This yields a solid which is filtered off, washed with acetone, rinsed and dried.

After recrystallisation from ethanol, a white solid is obtained.

Melting point=227°–229° C.

1.2  3-(2-Aminoethyl)-5-methyl-5-(4-fluorophenyl)-thiazolidine-2,4-dione hydrobromide.

9.6 g of the hydrobromide obtained above, 40 ml of water and 4 ml of concentrated hydrobromic acid are introduced into a 250 ml round-bottomed flask.

The mixture is heated under reflux for 6 hours. This yields a very light yellow, clear solution. The water is driven off in vacuo and a white solid is recovered.

Melting point=227°–228.5° C.

EXAMPLE 2
3-(2-Aminoethyl)-5-phenylthiazolidine-2,4-dione hydrobromide.

[$R_1=R_2=H$; $R_3=C_6H_5$; $R_4=H$]

1. 2-Phenyl-5,6-dihydroimidazo[2,1-b]thiazol[2H]-3-one hydrobromide.

10 g (0.098 mol) of ethylene-thiourea and 21.05 g (0.098 mol) of α-bromo-phenylacetic acid in 50 cm³ of acetic acid are introduced into a 250 cm³ round-bottomed flask.

The mixture is heated at 65°–75° C. for 4 hours. It is allowed to cool. The precipitate is filtered off and dried and then recrystallised from methanol.

The white solid obtained melts at 245°–247° C. with decomposition.

2. 3-(2-Aminoethyl)-5-phenylthiazolidine-2,4-dione hydrobromide.

15 g of the above hydrobromide, 20 cm³ of water and 4 cm³ of concentrated hydrobromic acid are introduced into a 100 cm³ round-bottomed flask. The mixture is heated under reflux for 4 hours and the water is then driven off under reduced pressure. This yields a white solid which is washed and recrystallised from ethanol.

Melting point=220°–222° C.

EXAMPLE 3
3-(2-Acetylaminoethyl)-5-phenylthiazolidine-2,4-dione.

[$R_1$=$CH_3CO$; $R_2$=H; $R_3$=$C_6H_5$; $R_4$=H]

3-(2-Aminoethyl)-5-phenylthiazolidine-2,4-dione is obtained from its hydrobromide (Example 2.2). It is a white solid which melts at 139.5°–140.5° C.

8.9 g (0.038 mol) of this base and 300 cm³ of dry pyridine are intoduced into a round-bottomed flask. The mixture is stirred for 30 minutes and 3.14 g (0.04 mol) of acetyl chloride are then added slowly, under argon.

After stirring for 2 hours, the pyridine is driven off. A yellow oil is recovered and taken up in chloroform. After washing and concentration, a light yellow oil is obtained, which crystallises immediately in ether. After recrystallisation from toluene, the white solid obtained melts at 136°–137° C.

EXAMPLE 4
3-(2-Aminoethyl)-5-methyl-5-phenylthiazolidine-2,4-dione hydrochloride.

[$R_1$=$R_2$=H; $R_3$=$CH_3$; $R_4$=$C_6H_5$]

4.1 2-Phenyl-2-methyl-5,6-dihydroimidazo[2,1-b]thiazol[2H]-3-one.

A solution in dry DMF (400 ml) of the compound obtained under 2.1, in the form of the free base (32.7 g, 0.15 mol), is added to sodium hydride which has been washed with pentane beforehand, whilst cooling in an ice bath. The addition is carried out in the course of 30 minutes under a nitrogen atmosphere. The suspension is stirred for 1 hour at ambient temperature and cooled in an ice bath and methyl iodide (21.3 g, 0.15 mol) is added dropwise in the course of 5 minutes.

The reaction mixture is stirred for 3 hours and the light red solution is poured into water. Extraction is carried out with ethyl acetate until the extracts are colourless; the extracts are washed with water and dried over $MgSO_4$. The mixture is filtered and evaporated and a yellow solid is obtained. After recrystallisation from a mixture of isopropyl ether and ethyl acetate, the solid melts at 102°–103.5° C.

4.2. 3-(2-Aminoethyl)-5-methyl-5-phenylthiazolidine-2,4-dione hydrochloride.

A suspension, in 80 ml of water, of the free base obtained above (see 4.1) (9.2 g, 0.04 mol) is acidified to pH 1-2 with 2 N hydrochloric acid.

The colourless solution is heated under reflux for 6 hours. The reaction medium is concentrated under reduced pressure. This yields a white solid which is recrystallised from ethanol.

Melting point=223°–224.5° C.

EXAMPLE 5
3-(2-Dimethylaminoethyl)-5-methyl-5-phenylthiazolidine-2,4-dione hydrochloride.

[$R_1$=$R_2$=$CH_3$; $R_3$=$C_6H_5$; $R_4$=$CH_3$]

A mixture of the compound obtained under 4.2 (12.6 g, 0.044 mol), formic acid (10.13 g, 0.22 mol) and formaldehyde (8.6 ml of a 35% strength solution, 0.01 mol) is heated at 100° C. for 12 hours.

The colourless solution is cooled and diluted with water and the mixture is washed with $CHCl_3$. It is rendered alkaline with $Na_2CO_3$ and extracted with $CHCl_3$.

The extracts are washed, dried over $MgSO_4$ and evaporated.

This yields an oil which is taken up and treated with $Et_2O$/HCl.

The white precipitate is filtered off and recrystallised from a mixture of EtOH and petroleum ether and then from methyl ethyl ketone.

Melting point=178.5°–179.5° C.

EXAMPLE 6
3-(2-Benzylaminoethyl)-5-methyl-5-phenylthiazolidine-2,4-dione hydrobromide.

[$R_1$=$C_6H_5CH_2$; $R_2$=H; $R_3$=$C_6H_5$; $R_4$=$CH_3$]

Benzyl bromide (5.13 g, 0.013 mol) is added to a solution in EtOAc (250 ml) of the compound obtained under 4.1 (6.96 g, 0.03 mol).

The mixture is heated under reflux for 5 days and the precipitate (A) of the formula

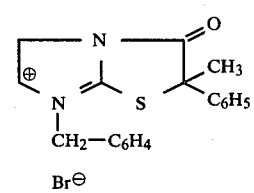

$Br^{\ominus}$ is filtered off.

A further amount of the compound A can be obtained by heating the filtrate for 5 days with 0.03 mol of benzyl bromide.

The compound A (9.3 g) is taken up in a mixture of ethanol and water (25/25 ml) and the mixture is heated under reflux for 4 hours. The light red solution is cooled, treated with charcoal and evaporated.

The white solid obtained by trituration is recrystallised from a mixture of ethanol and petroleum ether and then from a mixture of isopropanol and ethanol.

Melting point=169°–170.5° C.

EXAMPLE 7
3-(2-Methylaminoethyl)-5-phenylthiazolidine-2,4-dione hydrochloride.

[$R_1$=$CH_3$; $R_2$=H; $R_3$=$C_6H_5$; $R_4$=H]

Dimethyl sulphate (6.3 g, 0.05 mol) is added to a suspension in ethyl acetate (250 ml) of the compound obtained under 2.1 (10.9 g, 0.05 mol) and the mixture is heated under reflux.

The reaction mixture is cooled after 6 hours and filtered.

The methylsulphate melts at 161°–4° C.

The white crystalline product is dissolved in water (50 ml) and the solution is heated under reflux for 6 hours. The light yellow solution is brought to pH 2–3 and extracted with chloroform. The extracts are dried over $MgSO_4$ and evaporated and the oil is taken up in acetone. It is converted into the hydrochloride.

After recrystallisation from isopropanol and then from a mixture of ethanol and petroleum ether, a white solid is obtained.

Melting point=226.5°–228.5° C.

EXAMPLE 8
3-(2-Aminoethyl)-5-(naphth-1-yl)-thiazolidine-2,4-dione hydrobromide.

1.1 2-(Naphth-1-yl)-5,6-dihydroimidazo[2,1-b]thiazol[2H]-3-one hydrobromide.

42.4 g (0.415 mol) of ethylene-thiourea and 110 g (0.415 mol) of α-bromo-(naphth-1-yl)-acetic acid are introduced into a 1 liter round-bottomed flask.

The mixture is heated at 65°–75° C. for 4 hours. The solid obtained is filtered off and recrystallised from a mixture of methanol and water.

Melting point = 304°–306° C.

1.2 3-(2-Aminoethyl)-5-naphth-1-yl)-thiazolidine-2,4-dione hydrobromide.

12 g of the hydrobromide obtained under 1.1, 80 ml of water and 8 ml of HBr are introduced into a 250 ml round-bottomed flask. The mixture is heated under reflux for 6 hours. The solution obtained is concentrated in vacuo. The solid obtained is recrystallised from isopropyl alcohol.

Melting point = 142°–144° C.

EXAMPLE 9
3-(2-Aminoethyl)-5-(3,4-dichlorophenyl)thiazolidine-2,4-dione hydrobromide.

[$R_1 = R_2 = H$; $R_3 = 3,4$—$Cl_2$—$C_6H_3$; $R_4 = H$]

1.1 2-(3,4-Dichlorophenyl)-5,6-dihydroimidazo[2,1-b]thiazol[2H]-3-one hydrobromide.

2.0 g (0.02 mol) of ethylene-thiourea and 6.5 g (0.023 mol) of α-bromo-3,4-dichlorophenylacetic acid in 15 cm³ of acetic acid are introduced into a 250 cm³ round-bottomed flask. The mixture is heated at 65°–75° C. for 4 hours. After ½ hour, the solution becomes clear and then solidifies. A solid is recovered and rinsed with acetone.

Melting point = 265°–267° C. (decomposition).

1.2 3-(2-Aminoethyl)-5-(3,4-dichlorophenyl)-thiazolidine-2,4-dione hydrobromide.

6.2 g (0.0168 mol) of the hydrobromide, 60 cm³ of water and 3 cm³ of concentrated hydrobromic acid are introduced into a 250 cm³ round-bottomed flask. The mixture is heated at the reflux temperature for 6 hours until a clear colourless solution is obtained. It is concentrated in vacuo at 90° C. This yields a white solid. It is rinsed with hot ethyl acetate and filtered off. The white solid obtained is recrystallised from a mixture of acetone and ethanol (2/1) and then once again from ethanol.

Melting point = 226°–228° C.

The compounds of the invention, prepared by way of examples, are summarised in Table I which follows.

TABLE I

| Compound No. | $R_1$ | $R_2$ | $R_3$ | $R_4$ | n | Salt | Melting point (°C.) |
|---|---|---|---|---|---|---|---|
| 1 | H | H | $C_6H_5$ | H | 2 | HBr | 220–222 |
| 2 | $C_6H_5CO$ | H | $C_6H_5$ | H | 2 | — | 156–7 |
| 3 | $CH_3CO$ | H | $C_6H_5$ | H | 2 | — | 136–7 |
| 4 | H | H | $C_6H_5$ | H | 3 | HBr | 194–195.5 |
| 5 | H | H | $C_6H_5$ | $C_6H_5CH_2$ | 2 | $(CO_2H)_2 \cdot 1H_2O$ | 149–150 |
| 6 | H | H | $C_6H_5$ | $CH_3$ | 2 | HCl | 223–224.5 |
| 7 | H | H | $C_6H_5$ | $C_6H_5$ | 2 | HCl | 205–206.5 |
| 8 | H | H | 4-Cl—$C_6H_4$ | H | 2 | HBr | 184–185.5 |
| 9 | H | H | 4-MeO—$C_6H_4$ | H | 2 | HBr | 176–177.5 |
| 10 | H | H | 4-Cl—$C_6H_4$ | H | 3 | HBr | 183–5 |
| 11 | H | H | 4-MeO—$C_6H_4$ | H | 3 | HBr | 217–218.5 |
| 12 | $C_6H_5CH_2$ | H | $C_6H_5$ | H | 2 | $(CO_2H)_2$ | 227–228 |
| 13 | $CH_3$ | H | $C_6H_5$ | H | 2 | HCl | 226.5–228.5 |
| 14 | $CH_3$ | H | $C_6H_5$ | $CH_3$ | 2 | HCl | 162–163.5 |
| 15 | $C_6H_5CH_2$ | H | $C_6H_5$ | $CH_3$ | 2 | HBr | 169–170.5 |
| 16 | H | H | 4-F—$C_6H_4$ | H | 2 | HBr | 200–201.5 |
| 17 | H | H | 4-Br—$C_6H_4$ | H | 2 | HBr | 213–214.5 |
| 18 | $CH_3$ | $CH_3$ | $C_6H_5$ | $CH_3$ | 2 | HCl | 178–179.5 |
| 19 | H | H | 4-Cl—$C_6H_4$ | $CH_3$ | 2 | HCl | 204–5 |
| 20 | H | H | 4-Cl—$C_6H_4$ | $C_2H_5$ | 2 | HCl | 248.5–250 |
| 21 | H | H | 4-Cl—$C_6H_4$ | n-$C_3H_7$ | 2 | HCl | 250–2 |
| 22 | H | H | 4-Cl—$C_6H_4$ | $H_2C=CHCH_2$ | 2 | HCl | 228–9 |
| 23 | H | H | 4-F—$C_6H_4$ | $CH_3$ | 2 | HBr | 227–228.5 |
| 24 | H | H | Naphth-1-yl | H | 2 | HBr | 142–4 |
| 25 | H | H | 2-Cl—$C_6H_4$ | H | 2 | HBr | 226–227.5 |
| 26 | H | H | 4-$CH_3$—$C_6H_4$ | H | 2 | HCl.½$H_2O$ | 190–192.5 |
| 27 | H | H | 3-$CF_3$—$C_6H_4$ | H | 2 | HCl | 185–186.5 |
| 28 | H | H | 3-MeO—$C_6H_4$ | H | 2 | HCl | 218.5–220 |
| 29 | H | H | 3-$NO_2$—$C_6H_4$ | H | 2 | HCl | 216–217.5 |
| 30 | H | H | $C_6H_5$ | $C_2H_5$ | 2 | HCl | 202–203.5 |
| 31 | H | H | $C_6H_5$ | Iso-$C_3H_7$ | 2 | HCl.½$H_2O$ | 144–145.5 |
| 32 | H | H | $C_6H_5$ | n-$C_3H_7$ | 2 | HCl | 217–218.5 |
| 33 | $CH_3$ | $CH_3$ | Naphth-1-yl | H | 2 | HCl.½$H_2O$ | 213–215 |
| 34 | H | H | Naphth-1-yl | $CH_3$ | 2 | HCl.½$H_2O$ | 167.5–169 |
| 35 | $C_6H_5CH_2$ | H | Naphth-1-yl | H | 2 | HBr.½$H_2O$ | 190–1 |
| 36 | H | H | 3-Cl—$C_6H_4$ | H | 2 | HBr | 189–190.5 |
| 37 | $C_6H_5CH_2$ | H | 3-$CF_3$—$C_6H_4$ | H | 2 | HBr | 136–8 |
| 38 | H | H | 2,4-$Cl_2$—$C_6H_3$ | H | 2 | HBr | 216.5–218 |
| 39 | H | H | 3,4-$Cl_2$—$C_6H_3$ | H | 2 | HBr | 226–8 |
| 40 | H | H | 3-$CF_3S$—$C_6H_4$ | H | 2 | HBr | 162–3.5 |
| 41 | 2-$CH_3$—$C_6H_4CH_2$ | H | 3-$CH_3O$—$C_6H_4$ | H | 2 | HBr | 145.5–147 |
| 42 | H | H | 4-F-3-$CF_3$—$C_6H_3$ | H | 2 | HBr | 122–4 |
| 43 | $CH_3$ | H | 3,4-$Cl_2$—$C_6H_3$ | H | 2 | HCl | 249–251 |
| 44 | $CH_3$ | H | 3-$CF_3$—$C_6H_4$ | H | 2 | HCl | 181–3 |
| 45 | H | H | 2-Br-4,5-di-$CH_3O$—$C_6H_2$ | H | 2 | HCl | 216–8 |
| 46 | $C_2H_5$ | H | 3-$CF_3$—$C_6H_4$ | H | 2 | HCl | 147.5–9 |

The compounds of the invention were subjected to pharmacological experiments which showed an anticonvulsive activity and, in certain cases, an antidepressive activity.

The acute toxicity was determined intraperitoneally on mice. It varies from 200 to 1,000 mg/kg.

The anticonvulsive activity was determined by the test for the antagonism towards the convulsions induced by bicuculline in mice (M. Perez de la Mora and R. Tapia, Biochem. Pharmacol., 22, 2,635–2,639 (1973)).

The products to be studied are injected intraperitoneally, 30 minutes before the bicuculline (0.9 mg/kg, administered intravenously). The criterion adopted for this test is lethality and the percentage mortality is noted for each batch, 2 hours after administration of the bicuculline (control batch: 100% mortality).

For each product, the 50% active dose (AD 50 or the dose which protects 50% of animals from the lethal effects of the bicuculline) is determined graphically.

The AD 50 of the compounds of the invention, administered intraperitoneally, varies between 20 and 60 mg/kg.

The antidepressive activity was determined in accordance with the test for the antagonism towards the ptosis induced by reserpine (C. Gouret et al., J. Pharmacol. (Paris), 8, 333–350 (1977)).

The mice (male, CD1 Charles River, France, 18–22 g) simultaneously receive the products to be studied or the solvent (administered intraperitoneally) and the reserpine (4 mg/kg, administered subcutaneously).

Sixty minutes later, the degree of palpebral ptosis is estimated, for each mouse, by means of a rating scale (0 to 4).

The mean rating and the % variation relative to the control batch are calculated for each dose.

The AD 50, or the dose which reduces the mean ptosis score by 50%, relative to the controls, is determined graphically for each product.

The AD of the compounds of the invention ranges from 1.5 to 10 mg/kg. The results of the tests show that the compounds of the invention are anticonvulsive agents which are useful for treating various types of epilepsy, and antidepressants which are useful for treating depression.

The compounds of the invention can be presented in any form which is suitable for oral, parenteral or endorectal administration, for example in the form of tablets, dragees, sugar-coated pills, solutions which can be taken orally or injected, and the like, toether with any suitable excipient.

The daily dosage can range from 200 to 1,500 mg/kg for the anticonvulsive agents and from 5 to 200 mg for the antidepressants.

I claim:

1. A compound of the formula

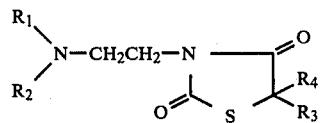

wherein $R_1$ is H, $CH_3$, $C_2H_5$, benzyl, 4-chlorobenzyl, or $CH_3CO$;

$R_2$ is H; $R_3$ is phenyl, 4-chlorophenyl, 4-fluorophenyl, 4-bromophenyl, 1-naphthyl, $3-CF_3-C_6H_4$, 3-methoxyphenyl, 3-chlorophenyl, 2,4-dichlorophenyl, 3,4-dichlorophenyl, 2-bromo-4,5-dimethoxyphenyl; and $R_4$ is H or $CH_3$ with the proviso that if $R_3$ is phenyl, $R_4$ is $CH_3$ or a pharmaceutically addition acceptable salt thereof.

2. A compound of claim 1 wherein $R_1$ is H.

3. A compound of claim 2 wherein $R_3$ is $3-CH_3-C_6H_4$, 2,4-dichlorophenyl, or 3,4-dichlorophenyl.

4. 3-(2-Aminoethyl)-5-(naphthyl)-thiazolidine-2,4-dione or a pharmaceutically acceptable salt thereof.

5. 3-(2-Aminoethyl)-5-(3-trifluoromethylphenyl-thiazolidine-2,4-dione) or a pharmaceutically acceptable salt thereof.

6. 3-(2-Aminoethyl)-5-(3,4-dichlorophenyl-thiazolidine-2,4-dione or a pharmaceutically acceptable salt thereof.

* * * * *